United States Patent
Kaufmann et al.

[11] Patent Number: 5,989,246
[45] Date of Patent: *Nov. 23, 1999

[54] PROBE FOR HEATING BODY TISSUE

[76] Inventors: Raimund Kaufmann; Hans-Joachim Schwarzmaier, both of Institut für Lasermedizin Universität Düsseldorf Universitätsstrasse 1, D-40225 Dusseldorf, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/362,430

[22] PCT Filed: Jun. 29, 1993

[86] PCT No.: PCT/EP93/01677

§ 371 Date: Feb. 9, 1995

§ 102(e) Date: Feb. 9, 1995

[87] PCT Pub. No.: WO94/00194

PCT Pub. Date: Jan. 6, 1994

[30] Foreign Application Priority Data

Jun. 29, 1992 [DE] Germany .............................. 42 21 364

[51] Int. Cl.[6] .................................................. A61B 17/36
[52] U.S. Cl. ............................................... 606/15; 607/89
[58] Field of Search ................................ 606/7, 9, 13–18, 606/27–31; 607/88–94, 154; 62/434

[56] References Cited

U.S. PATENT DOCUMENTS

| | | | |
|---|---|---|---|
| 1,550,197 | 8/1925 | Berry | 607/89 |
| 1,721,019 | 7/1929 | Hert | 607/154 |
| 2,074,034 | 3/1937 | Ackerman | 607/88 |
| 4,509,344 | 4/1985 | Ludwigsen et al. | 62/434 |
| 4,967,765 | 11/1990 | Turner et al. | 128/785 |
| 5,019,075 | 5/1991 | Speers et al. | 606/7 |
| 5,129,896 | 7/1992 | Hasson | 606/15 |
| 5,165,773 | 11/1992 | Nath | 606/15 |
| 5,169,396 | 12/1992 | Dowlatshahi et al. | 606/15 |
| 5,190,540 | 3/1993 | Lee | 606/27 |
| 5,196,005 | 3/1993 | Doiron et al. | 606/15 |
| 5,209,748 | 5/1993 | Daikuzono | 606/15 |
| 5,281,213 | 1/1994 | Milder et al. | 607/89 |
| 5,304,171 | 4/1994 | Gregory et al. | 606/15 |
| 5,415,654 | 5/1995 | Daikuzone | 606/15 |
| 5,441,497 | 8/1995 | Narciso, Jr. | 606/15 |

FOREIGN PATENT DOCUMENTS

| | | |
|---|---|---|
| 0370890 | 5/1990 | European Pat. Off. . |
| 0439629 | 8/1991 | European Pat. Off. . |
| 4137983 | 11/1991 | Germany . |

*Primary Examiner*—Robert L. Nasser
*Attorney, Agent, or Firm*—Fitch, Even, Tabin & Flannery

[57] ABSTRACT

The invention concerns a probe for heating body tissue by means of high-intensity laser light, the probe having an optical fibre coupled to a laser source and a diffusor element located in the light-exit zone which is inserted into the body tissue. The diffusor element is made of a material which is highly transparent to the laser light but which contains highly reflective particles embedded in it. The probe is connected to a coolant circuit to cool the light-exit zone.

21 Claims, 3 Drawing Sheets

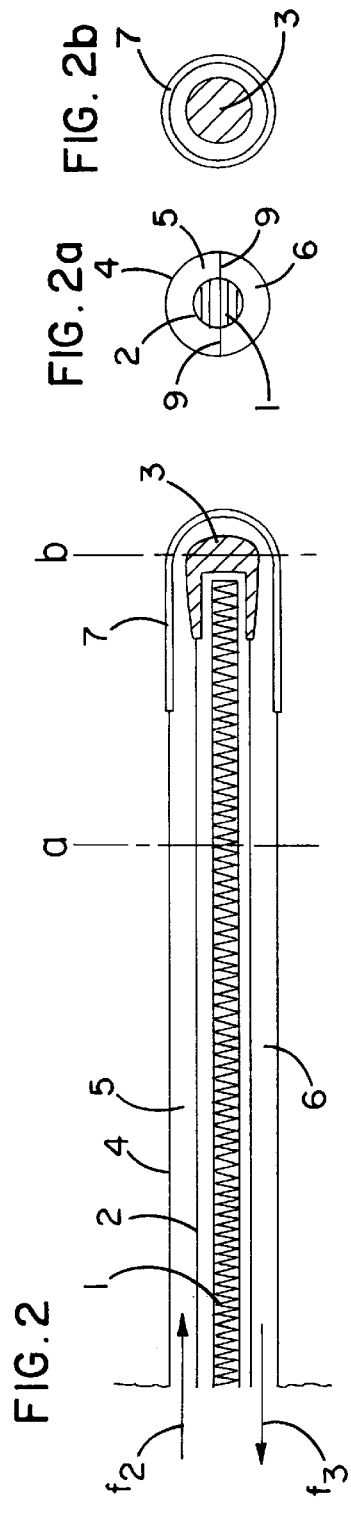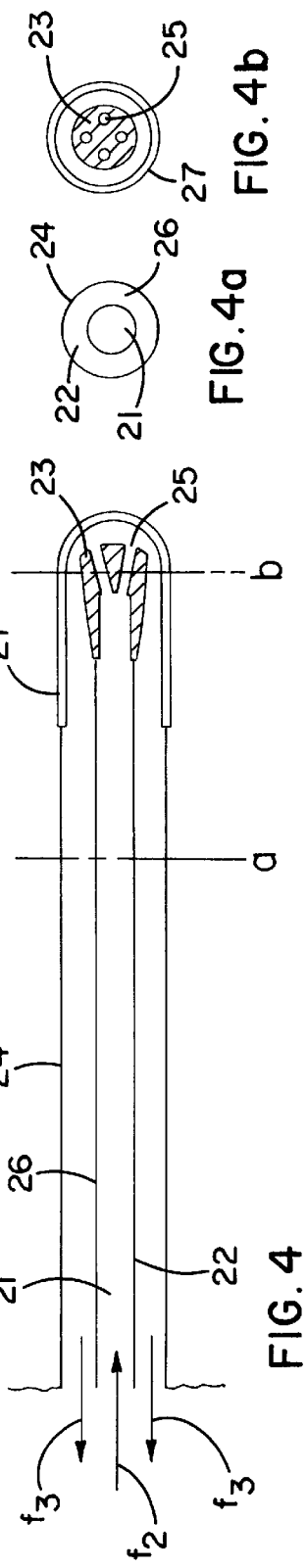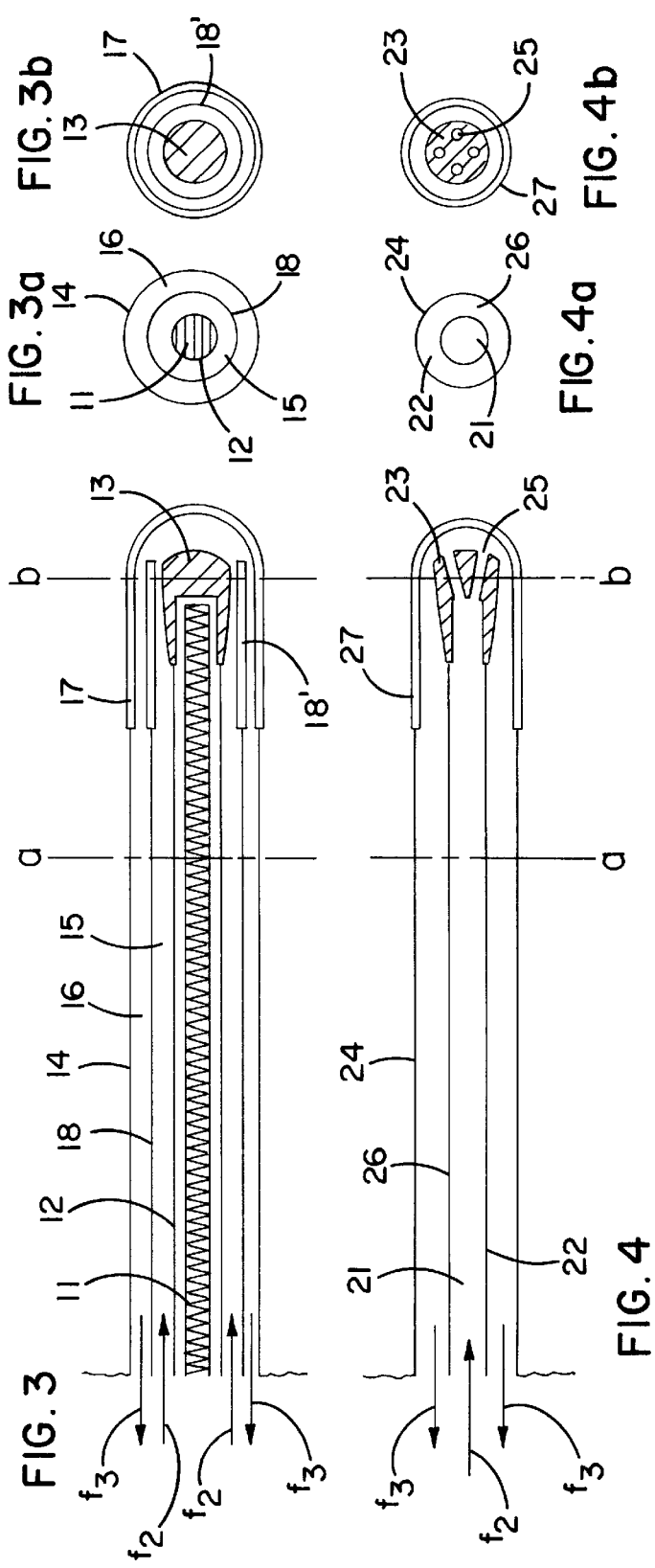

PROBE FOR HEATING BODY TISSUE

PROBE FOR HEATING BODY TISSUE

The invention relates to a probe for heating body tissue according to the generic part of claim 1.

Since 1983 (Bown S G, World J. Surg, 1983, 7, 700–709), lasers have been used for interstitial tumor therapy. The method intends to achieve a controlled, and, to the largest possible extent, homogeneous heating of sufficiently large tissue volumes (diameter>2 cm) by means of the introduction of light via light guides. The main advantage of the method consists in the fact that only a thin puncture channel (<2,55 mm) is necessary to give the surgeon access to the tumor. This minimally invasive technique is especially suited for treating deep-seated tumors which are inaccessible to other therapeutical methods. Since tumor cells are considered to be particularly sensitive to heat (Lambert A R; JAMA; 1912, 59, 2147–2148), a relatively slight increase in temperature by approximately 7° C. to 9° C. during a period of a few minutes is sufficient for destroying the tumor. It is therefore a pre-condition of successful "interstitial thermotherapy" that the tumor is heated by at least this temperature also in its peripheral areas.

When using conventional light guides for introducing energy (Bare Fiber; ITT-Faser® DE 38 13 227), however, an undesirable temperature profile is created in the tissue in that temperature decreases abruptly as tissue depth increases. As a consequence, a therapeutically effective temperature increase is only present in an area having a diameter of a few millimeters around the site of introduction (Masters A, Bown S G, Las. Med. Sci; 1990, 5, 129–136; Svaasand L O, et al., Las. Med. Sci; 1990, 5, 121–128). This is insufficient for treating most clinically relevant tumors. The radiation power can only be increased within narrow limits, since an increase may result not only in vaporization or carbonization of tissue, but subsequently also in the destruction of the fiber itself. The power output from a glass fiber (bare fiber) typically having a diameter of 600 μm is thus limited to a few Watt, which largely prevents therapeutic use of the principle in practice.

In principle, this problem could be somewhat diminished by increasing the diameter of the fiber and the output surface. This is in conflict, however, with the desired aim of keeping the outer diameter of the whole system as small as possible.

There have also been several attempts to solve the problem by using so-called diffusor elements specifically designed for the purpose. In general, these are intended to reduce the power density at the output site and, at the same time, ensure homogeneous solid angle distribution of the radiated energy. Hollow spherical or cylindrical diffusor elements are known whose cavities are in part filled with glass particles of a defined size (Heinze A, et al, SPIE; 1990, 1201, 304–312). For transmitting sufficiently high radiation energy, however, the output surface has to be enlarged to such an extent that the resulting increase in the size of the diffusor elements is inacceptable. A further problem is that the commonly used scattering particles put an additional heat load on the output portion due to their self-absorption. Materials for the isotropic scattering of laser light (e.g. Star W M, et al, Photochem. Photobiol.; 1987, 46, 5, 619–624) for high power densities at optical border surfaces (>7 kW/cm$^2$) have not yet been disclosed. Furthermore, there is as yet no possibility of varying the solid angle distribution of the radiated beam in a simple manner and according to choice. Likewise, the problem of the abrupt decrease in temperature within the tissue itself has not yet been solved. In principle, one could achieve a substantially homogeneous temperature distribution within a tissue volume by actively cooling the introduction surfaces. However, this means that a considerable portion of the total energy being introduced has to be removed again by active cooling. To achieve sufficient heating (increase in temperature by 7° C. to 9° C.) of a larger-sized tumor (diameter>2 cm), the transmissible laser power therefore has to be increased by at least one order of magnitude. This aggravates the problem of self-absorption of the diffusor element and the associated destruction threshold. So far, no diffusor elements have become known which can transmit the required total power (usually more than 30 W) while at the same time having the small outer diameter required for the intended purpose.

The problem to be solved by the invention consists in designing a probe of the above-mentioned type having a diffusor and output element whose dimensions are as small as possible such that in mean laser powers of at least 30 W, destruction of the output unit is securely prevented and a temperature increase is achieved which is as homogeneous as possible within the tissue to be heated in a radius of more than 10 mm around the probe, while temperatures which could lead to the vaporization or carbonization of tissue are securely prevented.

This problem is solved by the features cited in the characterizing part of claim 1.

A first essential feature of the solution according to the invention relates to the construction of the optical diffusor element. By embedding scattering particles which are highly reflective and therefore have an extremely low self-absorption into an optically transparent matrix, it is not only possible to transmit powers of 30 to 100 W, but it is also possible to achieve any desired radiation characteristic. In spite of the high power which can be transmitted, the outer diameter of the diffusor element can be limited to a maximum diameter of 1,5 mm. Particles of barium sulphate (refractive index n=1.6), magnesium oxide or aluminum powder are preferably used as the highly reflective material particles. The self-absorption of these particles is negligible. Their small size (<1 μm) permits a high particle concentration in the base material. The number of scattering processes for scattering the laser light in the desired solid angle (an isotropic scattering, for example) is ensured in spite of the fact that the geometrical dimensions of the diffusor element are limited.

Preferred highly transparent base materials include glass, glass-like substances, transparent adhesives or methyl acrylates (methyl methacrylate) having a refractive index of n=1.4. The latter material has a high transmission within the spectral regions relevant herein, namely the red and the near infrared spectral regions. The radiation characteristic of the diffusor element can still be varied during the manufacturing process, especially if plastic material is used as the base material, by varying the concentration of the scattering particles. In addition, the material can be formed into any desired shape prior to hardening. The materials forming at least the cap of the probe are preferably nuclear magnetic resonance compatible.

The second essential feature of the solution according to the invention relates to the integration of the diffusor element into a cooling system which, due to the fact that the material of the light exit portion of the tubular sleeve has a good heat conductivity, also cools the tissue surrounding the light exit portion. In spite of the fact that the available total diameter of the probe is small (<2.5 mm), the cooling system can be made sufficiently efficient to achieve a temperature decrease in the proximity of the fiber which is sufficient to create a substantially homogeneous temperature profile. For this purpose, 80% to 90% of the introduced laser energy have to be removed again via the cooling system. The tip is small and is shaped for puncturing solid tissue at its distal end. It is useful to utilize a coolant which can be cooled down to a temperature below 0° C., which has sufficient viscosity at low temperatures and which has a high heat capacity. Such a coolant could for example consist of a mixture of a 0.9% sodium chloride solution and alcohol or methanol.

Although at first sight it seems to be meaningless to again remove 80 to 90% of the introduced laser energy by cooling, it is exactly this measure which ensures that even at a relatively large distance from the probe, the tissue can be heated without vaporizing or carbonizing tissue in the immediate proximity of the probe and without destroying the probe itself. Since a large portion of the heat transmissible by heat conduction is removed again via the cooling system, the heating of the tissue surrounding the probe is achieved primarily through radiation absorption. The effective temperature distribution in the tissue volume surrounding the probe can be seen as the result of two processes which are superimposed one upon the other, as will be explained in detail later on. The present invention makes use of the fact that, if suitable wavelengths are chosen, due to the relatively large penetration depth of the laser radiation the spacetime-integrals for the amount of heat introduced by radiation and for the amount of heat removed by heat conduction are not mirror-symmetrical. If one depicts these processes versus the radial distance from the probe in the tissue, and if the energy supply and the energy removal are appropriately dimensioned, the result will be a temperature-space profile which in a first approximation extends relatively flat over relatively large tissue volumes. By optimizing the radiation characteristic in combination with laser light suited wave lengths and the use of an efficient cooling system, the present invention optimizes the temperature-space profile such that the tumor tissue volume which is effectively destroyed by the rise in temperature is increased by a factor of at least 3 to 4, while, at the same time, an undesirable overheating of the tip of the probe is prevented.

According to a particularly preferred embodiment, the light guide is hollow and is surrounded by a spaced apart outer sleeve, which is transparent and has good heat conductivity at least in the area of the diffusor element, wherein the diffusor element is porous, so that the cavity of the light guide and the space between the light guide and the outer sleeve form a passageway for the coolant. The particular advantage of this solution consists in that the coolant simultaneously functions as a light guide. This allows a particularly compact construction of the probe.

Another solution, which also allows to construct a probe of a particularly small diameter consists in surrounding the light guide with a spaced apart outer sleeve which is transparent and has good heat conductivity at least in the area of the diffusor element, and which is divided into at least two channels by means of a membrane extending in parallel to the axis, said two channels communicating with each other in the area of the free probe end.

According to a third embodiment, the light guide is surrounded by two coaxial outer sleeves to form a first channel between the light guide and the radially inner sleeve and a second channel between the two sleeves, wherein the two sleeves are transparent and have good heat conductivity at least in the area of the diffusor element, and wherein the two channels communicate in the area of the free probe end. This solution permits a high flow rate of coolant. In each embodiment, the sleeves surrounding the light guide can either be rigid or flexible, wherein the material of the outer sleeve can be comprised of a tension and pressure resistant plastic which is heat-resistant within wide ranges and which has poor heat conductivity except for the transparent area.

If the diffusor element is arranged at the tip of the probe, the tip is conveniently formed of a transparent cap which accommodates the diffusor element which is surrounded by the flowing coolant. To ensure optimal heat transport, the cap itself is most preferably made of a diamond. A sapphire cap, although having good heat conductivity also, is not suitable due to its self-absorption for wavelengths which penetrate deeply into biological tissue (red and near infrared spectral region). For economical reasons, the cap will usually be formed of quartz glass or similar types of glass.

The heat conductivity thus having been defined, the maximum amount of removable heat now only depends on the temperature difference between the tissue and the cooling liquid ($\Delta T$). If it is assumed, for example, that the surface of the cap is 30 mm$^2$ and the thickness of the glass wall is 0.3 mm, the removal of 27 W, e.g., requires a minimum temperature difference ($\Delta T$) of about 20° C.

A temperature difference between the tissue and the coolant of about 20 to 30° C., however, is not enough for destroying large tissue volumes. Rather, the temperature at the fiber has to be lowered to such an extent that the temperature profile created by the removal of heat allows a maximum of energy introduction by radiation. Therefore, the tissue close to the fiber should in general be cooled down to a temperature below 0° C.

The coolant can be a liquid or a gas, wherein a closed cooling circuit can be provided for the coolant flowing through the probe, which circuit is connected to a secondary cooling circuit via a heat exchanger. Also the expansion of a gas in the area of the diffusor element can be used for cooling.

Further features of the invention can be taken from the further subclaims and the following specification which illustrates the invention on the basis of embodiments thereof in connection with the attached drawings, wherein FIG. 1 is a schematic view of the probe together with the laser light source and the cooling system;

FIG. 2 is a schematic sectional view of the portion of the probe near the probe tip according to a first embodiment of the invention, wherein the cutting plane contains the probe axis;

FIG. 2a is a schematic cross-section along line a—a in FIG. 2;

FIG. 2b is a schematic cross-section along line b—b in FIG. 2;

FIGS. 3, 3a, 3b are illustrations of a second embodiment of the invention corresponding to FIGS. 2, 2a, 2b;

FIGS. 4, 4a, 4b are illustrations of a third embodiment of the invention corresponding to FIGS. 2, 2a, 2b;

Figure 1:
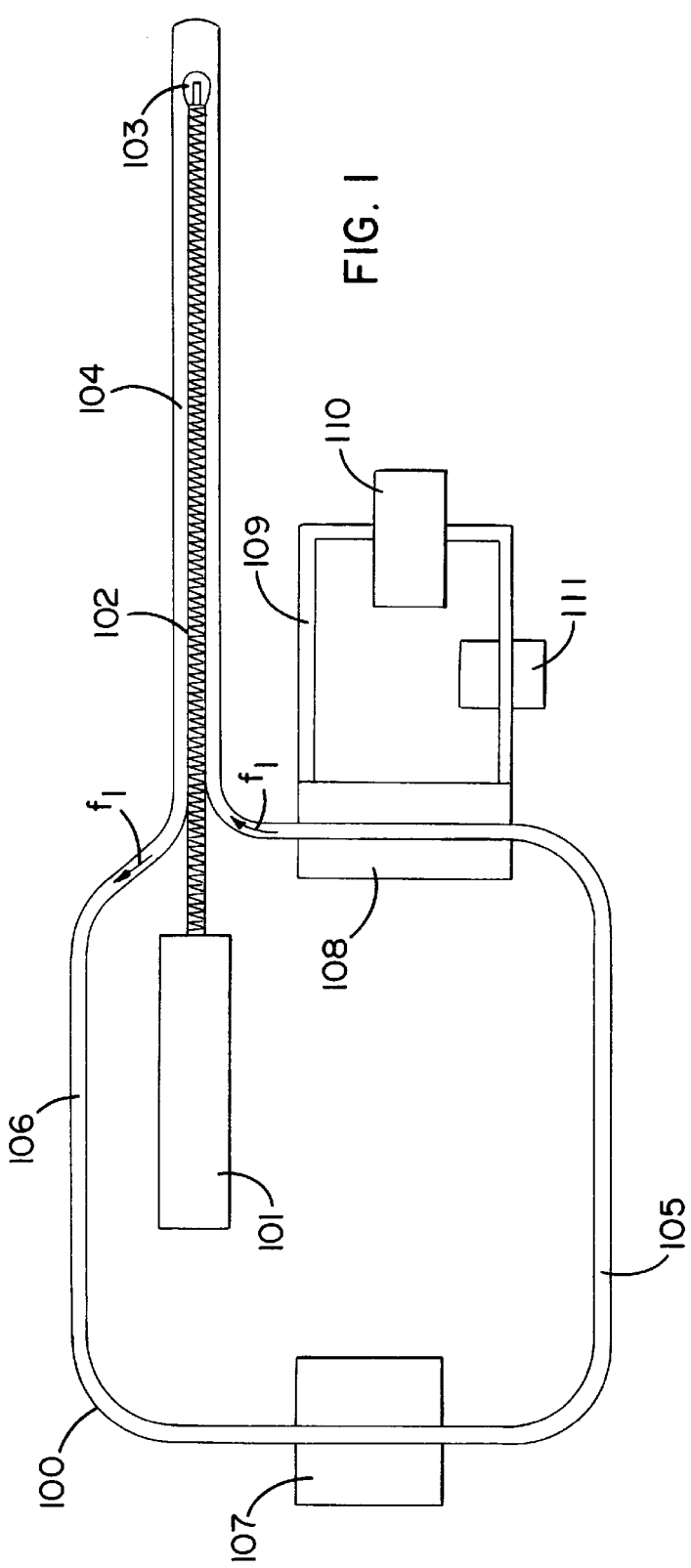

FIG. 1 shows a laser system 100 for heating large volumes of tissue and especially for destroying tumor tissues by heating. The laser system comprises a laser light source 101 having a light guide 102 coupled thereto. The light guide ends in a diffusor element 103 which is surrounded by a coolant circuit 104 having a supply 105 and a drain 106. A pump 107 causes the coolant to circulate within this closed coolant circuit in the direction of the arrows f1. The coolant is kept at a constant desired temperature by means of a heat exchanger 108. The heat exchanger 108 is further arranged in a second cooling circuit 109 having a pump 110 which drives the coolant in the secondary circuit 109 towards a compressor 111.

A first embodiment of a laser probe or a laser catheter according to the invention is shown in longitudinal section and in cross-section in FIGS. 2, 2a and 2b.

The light guide 1 and its sheath 2 end in a diffusor element 3. The coolant circuit is realized by means of an outer sleeve 4. The space created between the fiber sheath 2 and the outer sleeve 4 is divided into a supply 5 and a drain 6 by two membranes 9 extending in parallel to the axis. In the area of the diffusor element 3, the outer sleeve 4 ends in a transparent cap 7. The membranes 9 end in this area, so that the diffusor element is surrounded by the flowing coolant. The arrows f2 and f3 show the flowing direction of the coolant in the supply and in the drain of the catheter.

In the embodiment shown in FIGS. 3, 3a and 3b, the light guide 11 and its sheath 12 also end in a diffusor element 13. In this embodiment, the coolant circuit is realized by means of two additional sleeves. In this case, the space 15 between the fiber sheath 12 and the radially inner sleeve 18 serves as the supply. The space 16 between the inner sleeve 18 and the outer sleeve 14 forms the drain. The cover cap 17 and the distal part 18' of the inner sleeve 18 are formed of a transparent material. Again, the arrows f2 and f3 indicate the direction of coolant flow in the supply and drain.

A particularly preferred embodiment of the invention is shown in FIGS. 4, 4a and 4b. The light guide 21 is in this case designed as a liquid light guide and itself serves as the coolant supply. Thus, the coolant is at the same time the light guiding medium. The coolant then flows through the diffusor element 23 and leaves it through exit openings 25. The draining of the coolant from the transparent cap 27 is achieved via a cavity 22 which is defined by the fiber sheath 26 and the outer sleeve 24. Again, the arrows f2, f3 indicate the direction of liquid supply and drain.

Figure 5C:
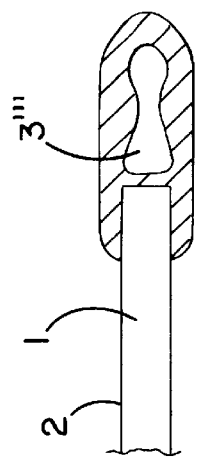
FIGS. 5a, 5b, 5c are schematic sectional views of three embodiments of a diffusor element, wherein the cutting plane contains the probe axis.
Figure 5B:
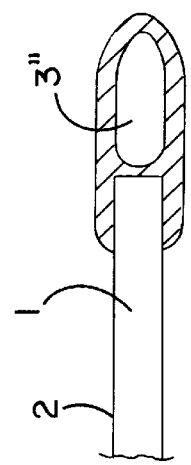
Figure 5A:
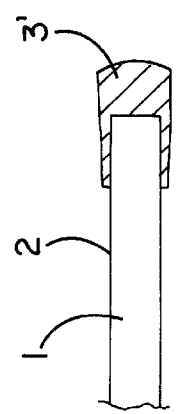

FIGS. 5a, 5b and 5c each show the end of a light guide 1 having a sheath 2 and a diffusor element 3', 3" or 3'", shown in schematic view. The Figures show that the diffusor element can have different shapes adapted to produce different radiation characteristics. In addition, the distribution of the scattering particles, indicated by black dots, within the transparent base material into which they are embedded, may be non-homogeneous.

Figure 6:
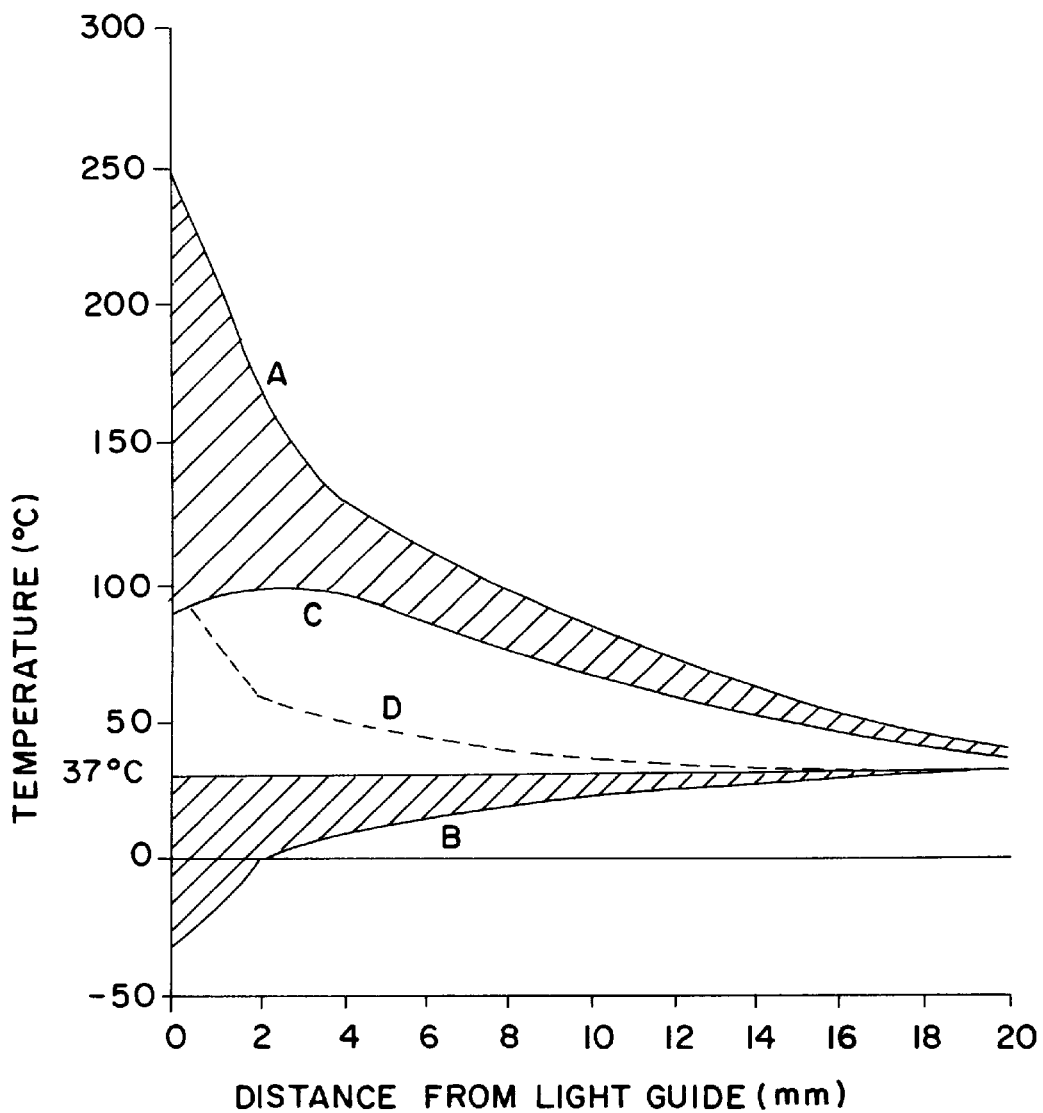
FIG. 6 is a graphic illustration of temperature-space profiles in the tissue.

Finally, FIG. 6 is a graph showing temperature-space profiles in a tissue into which the probe of the invention has been introduced, wherein the temperature (ordinate) is shown versus the radial distance from the light guide (abscissa). Curve A is the temperature profile produced by the introduction of radiation alone. Curve B shows the temperature profile produced by cooling alone. Curve C is the temperature profile resulting from the superimposed effects of A and B in the tissue. For better comparison, curve D (dotted line) shows the temperature profile in the tissue with an uncooled bare fiber.

It will be appreciated that even in the immediate proximity of the light guide, the temperature does not rise above 100° C. Nevertheless, even at a distance of 20 mm from the light guide, there is still a notable increase in temperature.

We claim:

1. A probe for heating body tissue by high-intensity laser light from a laser light source, said probe comprising:
    a light guide for coupling to the laser light source and having an exit portion to be introduced into the body tissue;
    a diffuser element on the light guide made of a base material which is highly transparent to laser light;
    particles of material highly reflective to laser light embedded in the base material;
    a tubular sleeve surrounding and spaced from the light guide at a predetermined distance;
    the tubular sleeve having a cap at an end thereof being made of a material that is transparent to laser light and has good heat conductivity in the area of the diffuser element to transmit heat by conduction and by radiation to the body tissue;
    the diffuser element being spaced from the cap and surrounded by coolant with coolant between the cap and the diffuser element;
    the cap allowing isotropic scattering of laser light from the diffuser element; and
    means including a closed coolant passageway in the tubular sleeve having a channel for flowing coolant through the tubular sleeve toward the body tissue and surrounding the diffuser element to remove a substantial portion of the heat transmitted to the body tissue by heat conduction and from the body tissue, while the laser light source is being operated to produce heat radiation for tumor therapy.

2. A probe according to claim 1, wherein the particles of highly reflective material are selected from the group consisting of barium sulphate, magnesium oxide and aluminum powder.

3. A probe according to claim 1 wherein the diffuser element material is selected from the group comprising glass, glass-like plastics, transparent adhesives and methyl acrylates.

4. A probe according to claim 1 wherein the particles of highly reflective material are homogeneously distributed in the transparent material.

5. A probe according to claim 1 wherein the particles of highly reflective material are distributed non-homogeneously in said transparent material dependent on a desired radiation characteristic.

6. A probe according to claim 1 wherein said diffuser element is shaped to produce an approximately spherical heat radiation characteristic.

7. A probe according to claim 1 wherein said diffuser element is shaped to produce an approximately cylindrical heat radiation characteristic.

8. A probe according to claim 1 wherein said light guide is hollow and has coolant flowing therein, said light guide and said outer sleeve being spaced to form the passageway for the coolant to flow.

9. A probe according to claim 1 wherein the tubular sleeve has a free probe end, a membrane divides the passageway in the tubular sleeve into at least two channels extending in parallel to the axis, and wherein said channels communicate in the area of the free probe end.

10. A probe for heating body tissue by high-intensity laser light from a laser light source, said probe comprising:
    a light guide for coupling to the laser light source and having an exit portion to be introduced into the body tissue;
    a diffuser element on the light guide made of a base material which is highly transparent to laser light;

particles of material highly reflective to laser light embedded in the base material;

a tubular sleeve surrounding and spaced from the light guide at a predetermined distance;

the tubular sleeve being made of a material that is transparent to laser light and has good heat conductivity in the area of the diffuser element to transmit heat by conduction and by radiation to the body tissue; and means including a closed coolant passageway in the tubular sleeve having a channel for flowing coolant through the tubular sleeve toward the body tissue to remove a substantial portion of the heat transmitted to the body tissue by heat conduction and from the body tissue while the laser light source is being operated to produce heat radiation for tumor therapy;

the tubular sleeve having a free probe end, an inner coaxial sleeve having a radially inner and outer sleeve, the radially inner sleeve surrounding the light guide and forming a first channel portion between said inner sleeve and said light guide and a radially inner one of said sleeves, and a second channel portion being formed between the two sleeves; the two sleeves being transparent and have good heat conductivity at least in the area of the diffuser element, and wherein said two channel portions communicate in the area of the free probe end.

11. A probe according to claim 10 wherein in that the tubular sleeves surrounding the light guide are rigid tubes.

12. A probe according to claim 1 wherein the outer sleeve surrounding the light guide is flexible.

13. A probe according to claim 1 wherein the coolant has a sufficient viscosity to flow even at temperatures below 0° C.

14. A probe according to claim 13 further comprising said coolant which is a mixture of a 0.9% sodium chloride solution and alcohol or methanol.

15. A probe according to claim 1, wherein the materials forming at least the cap of the probe are nuclear magnetic resonance-compatible.

16. A probe according to claim 1 wherein a tip on the probe is adapted for puncturing solid tissue at its distal end.

17. A probe according to claim 1 wherein the cap of the tubular sleeve is made of diamond or quartz glass.

18. A method of heating body tissue with a probe receiving high-intensity laser light from a light source, said method comprising the steps of:

inserting the probe into the tissue;

generating the laser light and transmitting the laser light through a light guide to a diffuser element at an exit end of the probe, the probe at the diffuser element being less than about 2.5 mm in diameter;

applying at least 30 watts of power to the light guide probe;

scattering the laser light in a desired solid angle from the diffuser element to the tissue;

surrounding the diffuser element with coolant to cool the exit end of the probe;

cooling the exit end of the probe and the tissue in contact therewith with a coolant that removes more than one-half of laser energy thereby removing a large portion of the heat that would be transmitted by conduction to the tissue in the immediate vicinity of the diffuser element; and heating the tissue primarily by radiation to a temperature increase of at least 7° C. for tumor therapy.

19. A method in accordance with claim 18 including a cooling system and removing about 80% or more of the laser energy.

20. A method in accordance with claim 18 including the step of cooling the temperature of the tissue close to the diffuser element down to about 0° C.

21. A method in accordance with claim 18 including the steps of providing power in the range of 30 watts to 100 watts, and removing about 80% to 90% of the power by the coolant.

* * * * *